(12) United States Patent
Taoka et al.

(10) Patent No.: US 6,174,707 B1
(45) Date of Patent: Jan. 16, 2001

(54) PROCESS FOR PRODUCING L-ALLYSINE ACETALS

(75) Inventors: Naoaki Taoka, Kobe; Takehiko Matsumoto, Hameji; Kenji Inoue, Kakogawa, all of (JP)

(73) Assignee: Kaneka Corporation, Osaka (JP)

( * ) Notice: Under 35 U.S.C. 154(b), the term of this patent shall be extended for 0 days.

(21) Appl. No.: 09/202,901

(22) PCT Filed: Apr. 22, 1998

(86) PCT No.: PCT/JP98/01830

§ 371 Date: Mar. 4, 1999

§ 102(e) Date: Mar. 4, 1999

(87) PCT Pub. No.: WO98/48040

PCT Pub. Date: Oct. 29, 1998

(30) Foreign Application Priority Data

Apr. 22, 1997 (JP) ................................... 9-120341

(51) Int. Cl.[7] .............................. G01N 38/53; C12Q 1/30; C07D 319/06; C07C 62/06
(52) U.S. Cl. .............................. 435/75; 435/27; 435/135; 435/136; 435/264; 549/373; 562/566
(58) Field of Search ............................. 435/27, 266, 391, 435/135, 136, 74; 562/566; 549/373

(56) References Cited

U.S. PATENT DOCUMENTS 4,376,864 * 3/1983 Drauz et al. ..................... 549/373

OTHER PUBLICATIONS

L.J. Fowler et al ; In vitro studies on enzymic biosynthesis of the collagen crosslinks; Biochemical and Biophysical Research Communications vol. 41(1); pp. 251–259, Sep. 7, 1970.*
Caplus Abstract 1971:430105, Biochemistry, 1971 vol. 10(21); Nimni Marcel et al., Dec. 1971.*

* cited by examiner

Primary Examiner—Alan L. Rotman
Assistant Examiner—Rita Desai
(74) Attorney, Agent, or Firm—Pollock, Vande Sande & Amernick

(57) ABSTRACT

The present invention has for its object to provide a method for producing an L-allysine acetal which involves a fewer steps and is efficient.

This invention relates to method for producing an L-allysine acetal which comprises;

converting a D,L-allysine acetal of the following general formula (1) (wherein $R^1$ and $R^2$ are the same or different, and each of them represents an alkyl group having 1 to 8 carbon atoms, or they combinedly form a ring and represent an alkylene group having 2 to 8 carbon atoms) to a mixture of a 2-oxo-6,6-dialkoxyhexanoic acid of the following general formula (2) (wherein $R^1$ and $R^2$ are as defined above) and an L-allysine acetal of the following general formula (3) (wherein $R^1$ and $R^2$ are as defined above) by reacting in the presence of an enzyme capable of stereoselective oxidative deamination of D-amino acids and;

isolating said L-allysine acetal after said converting.

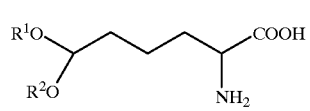

(1)

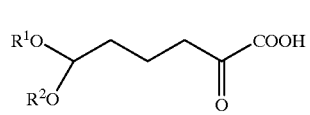

(2)

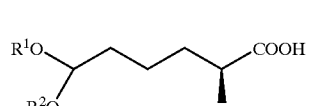

(3)

12 Claims, No Drawings

PROCESS FOR PRODUCING L-ALLYSINE ACETALS

This application is a 371 of PCT/JP98/01830 filed Apr. 22, 1998.

TECHNICAL FIELD

The present invention relates to a method for producing an L-allysine acetal. More particularly, the present invention relates to a method for producing L-allysine ethylene acetal. L-allysine ethylene acetal is of use as a synthetic intermediate in the production of medicinal substances.

BACKGROUND ART

Never known heretofore is a production technology for L-allysine acetals. All that is known is a process for producing the racemic compound D,L-allysine ethylene acetal which comprises 8 reaction steps starting with dihydropyran (Bioorganic & Medicinal Chemistry, (3)9, 1237 (1995)). However, this racemic compound cannot be utilized as a synthetic intermediate in the production of medicinal substances.

SUMMARY OF THE PRESENT INVENTION

In view of the above state of the art, the present invention has for its object to provide a method for producing an L-allysine acetal which involves a fewer steps and is efficient.

The present invention is directed to a method for producing an L-allysine acetal which comprises;
converting a D,L-allysine acetal of the following general formula (1):

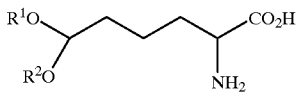

(1)

(wherein $R^1$ and $R^2$ are the same or different, and each of them represents an alkyl group having 1 to 8 carbon atoms, or they combinedly form a ring and represent an alkylene group having 2 to 8 carbon atoms) to a mixture of a 2-oxo-6,6-dialkoxyhexanoic acid of the following general formula (2):

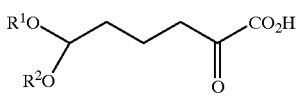

(2)

(wherein $R^1$ and $R^2$ are as defined above) and an L-allysine acetal of the following general formula (3):

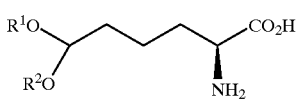

(3)

(wherein $R^1$ and $R^2$ are as defined above) by reacting in the presence of an enzyme capable of stereoselective oxidative deamination of D-amino acids and;
isolating said L-allysine acetal after said converting.

DETAILED DESCRIPTION OF THE PRESENT INVENTION

The present invention is now described in detail.

The D,L-allysine acetal for use in the present invention is a compound of the following general formula (1).

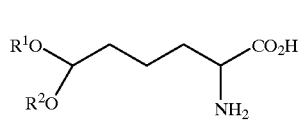

(1)

Referring to the D,L-allysine acetal of the above general formula (1), $R^1$ and $R^2$ are the same or different, and each of them represents an alkyl group having 1 to 8 carbon atoms, or they combinedly form a ring and represent an alkylene group having 2 to 8 carbon atoms. The alkyl group mentioned above is not particularly restricted but includes lower alkyl groups such as methyl, ethyl, propyl, isopropyl, n-butyl, isobutyl, t-butyl, s-butyl, hexyl, and octyl. The alkylene group mentioned above is not particularly restricted, either, but includes lower alkylene groups such as ethylene, trimethylene, tetramethylene, ethylethylene, butylethylene, and hexylethylene. In the present invention, use of D,L-allysine ethylene acetal in which $R^1$ and $R^2$ represent ethylene is preferred.

The D,L-allysine acetal of the above general formula (1) can be synthesized from dihydropyran, which is commercially available, in 8 steps by the method described in Bioorganic & Medicinal Chemistry, (3)9, 1237 (1995). In the alternative process disclosed in Japanese Kokai Publication Sho-48-39416, the objective compound can be easily produced by synthesizing glutaraldehyde monoethylene acetal from glutaraldehyde and ethylene glycol, both of which are commercially available, reacting said glutaraldehyde monoethylene acetal with potassium cyanide and ammonium carbonate in accordance with the well-known Bucherer method, and hydrolyzing the reaction product.

An enzyme capable of stereoselective oxidative deamination of D-amino acids for use in the present invention is not restricted but includes enzymes available from various sources, for example the D-amino acid oxidase derived from a strain of microorganism of the genus Trigonopsis, porcine kidney, and the like.

The above-mentioned D-amino acid oxidase of the Trigonopsis origin may for example be to "D-AOD Immobilized" (Boehringer Mannheim) and the like and the D-amino acid oxidase derived from porcine kidney includes "D-Amino Acid Oxidase" (Sigma).

The L-allysine acetal production method for the present invention can be typically carried into practice in the following manner.

The D,L-allysine acetal is dissolved in a buffer of pH 5 to 10, preferably pH 6 to 9, and concentration of 1 mM to 1 M, preferably 10 mM to 100 mM, at a substrate concentration of 0.1 to 50 w/v %, preferably 1 to 20 w/v %. To this solution is added 0.001 to 10 parts by weight, preferably 0.01 to 2 parts by weight, based on D,L-allysine acetal, of D-amino acid oxidase, and the D-selective oxidative deamination reaction is conducted under stirring at a reaction temperature of 5 to 80° C., preferably 10 to 50° C., for 1 to 100 hours, preferably 1 to 20 hours. After completion of the reaction, the D-amino acid oxidase is recovered with filtration or centrifugation and the pure L-allysine acetal is isolated by crystallization and the like technique.

The buffer mentioned above is not particularly restricted but includes a phosphate buffer and the like.

The solvent for said crystallization is not particularly restricted but includes alcoholic solvents such as methanol, ethanol, propanol, etc., water, and solvent mixtures thereof.

In the above oxidative deamination reaction, hydrogen peroxide usually is formed as a byproduct because molecular oxygen is the hydrogen acceptor of D-amino acid oxidase. It is known that accumulation of hydrogen peroxide inactivates enzymes and triggers decomposition of 2-oxo-6,6-dialkoxyhexanoic acids. The hydrogen peroxide produced in the course of catalysis by the D-amino acid oxidase can be eliminated by any of several alternative procedures known to those skilled in the art.

The first procedure involves use of the enzyme catalase. Thus, in the L-allysine acetal production method for the present invention, the disproportionation reaction of hydrogen peroxide to molecular oxygen and water can be catalyzed by conducting the reaction in the presence of a catalase.

As the catalase mentioned above, commercial products derived from mammalian livers, *Aspergillus niger* and the like are available.

The second procedure involves use of a metal oxide. Thus, in the L-allysine acetal production method for the present invention, the hydrogen peroxide can be decomposed by conducting the reaction in the presence of a metal oxide.

The above-mentioned metal oxide is not particularly restricted but includes manganese oxides such as manganese dioxide. The manganese oxides lead enzymes inclusive of said D-amino acid oxidase and catalase to stabilize and, as such, can be used with advantage.

In accordance with the present invention, said enzyme capable of stereoselective oxidative deamination of D-amino acids and said catalase may respectively be used in the form of whole cells containing them, crude disrupted cell preparations, partially purified cellular fractions, or purified enzymes. The enzymes may also be used either as they are or as immobilized beforehand.

BEST MODE FOR CARRYING OUT THE PRESENT INVENTION

The following examples are intended to illustrate the present invention in further detail without limiting the scope of the present invention in any manner.

EXAMPLE 1

A 15 mL screw tube was charged with 19 mg of D,L-allysine ethylene acetal, 19 mg of D-amino acid oxidase (derived from porcine kidney, Sigma), 2 mg of catalase (derived from bovine liver, Sigma), and 2 mL of 100 mM phosphate buffer (pH 8.3), and the reaction was carried out with stirring at room temperature for 22 hours. This reaction mixture was filtered and the filtrate was analyzed by HPLC (Finepak SIL C18-5, Nippon Bunko). The substrate residue rate was found to be 62%. The remaining L-allysine ethylene acetal was N-protected and methyl-esterified to give methyl 2-N-carbobenzyloxy-amino-6,6-ethylenedioxy-hexanoate, and it was then subjected to HPLC analysis (CHIRALCEL OD-H, Daicel). As a result, the optical purity of the product was found to be 85.6% e.e.

EXAMPLE 2

A 15 mL screw tube was charged with 19 mg of D,L-allysine ethylene acetal, 19 mg of immobilized D-amino acid oxidase (of the Trigonopsis origin, Boehringer Mannheim), 2 mg of catalase (derived from bovine liver, Sigma), and 2 mL of 100 mM phosphate buffer (pH 8.3) and the reaction was carried out with stirring at room temperature for 22 hours. This reaction mixture was filtered and the filtrate was subjected to HPLC analysis (Finepak SIL C18-5, Nippon Bunko). As a result, the substrate residue rate was found to be 49%. The remaining L-allysine ethylene acetal was N-protected and methyl-esterified to methyl 2-N-carbobenzyloxy-amino-6,6-ethylenedioxy-hexanoate, and it was then subjected to HPLC analysis (CHIRALCEL OD-H, Daicel). The optical purity was found to be 100% e.e.

EXAMPLE 3

In a 200 mL microjar, 4.73 g of D,L-allysine ethylene acetal and 4.1 mg of catalase (derived from bovine liver, Sigma) were dissolved in 100 mL of 10 mM phosphate buffer (pH 8.3). Then, 2.37 g of immobilized D-amino acid oxidase (of the Trigonopsis origin, Boehringer Mannheim) was added and the reaction was conducted with stirring and 0.5 mL/min. aeration at 25° C. for 12 hours. This reaction mixture was filtered and the filtrate was subjected to HPLC analysis. The substrate residue rate was 50%. The filtrate was also concentrated under reduced pressure, added methanol, and stirred under cooling with ice bath, and the precipitated L-allysine ethylene acetal was collected by filtration and dried to provide 1.73 g of pure L-allysine ethylene acetal. By HPLC analysis, the chemical purity of this product was found to be 99% (Finepak SIL C18-5, Nippon Bunko), and the optical purity was 100% e.e. (CROWNPAK CR(+), Daicel).

REFERENCE EXAMPLE 1

Synthesis of D,L-allysine ethylene acetal

In a 2 L three-necked flask, crude glutaraldehyde monoethylene acetal (486 mM, 74 mM of glutaraldehyde content) was dissolved in 350 mL of water, followed by addition of 72.6 g of sodium hydrogensulfite, and the mixture was stirred under cooling with ice bath for 1 hour. Then, 45.4 g of potassium cyanide was added and the reaction was carried out with stirring for 16 hours. After completion of the reaction, the organic layer was separated and the remaining aqueous layer was extracted with methylene chloride. The extract and said organic layer were combined and concentrated. The residue was dissolved in 350 mL of water –175 mL of ethanol, followed by addition of 112 g of ammonium carbonate, and the reaction was carried out at 55° C. for 20 hours. This reaction mixture was concentrated under reduced pressure and the ethanol was distilled off. Then, 875 mL of water and 349 g of barium hydroxide hydrate were added and the reaction was carried out under atmospheric pressure at 121° C. for 6 hours. Then, 85 g of ammonium carbonate was added and the precipitated barium carbonate was filtered off. The filtrate was concentrated, added methanol, and stirred under cooling. The precipitated crystal was recovered with filtration and dried to provide 73.6 g of pure D,L-allysine ethylene acetal (yield 80%).

INDUSTRIAL APPLICABILITY

The L-allysine acetal production method for the present invention being as described above, L-allysine acetals can now be produced in a fewer steps and with high efficiency.

What is claimed is:

1. A method for producing an L-allysine acetal which comprises;

converting a D,L-allysine acetal of the following general formula (1):

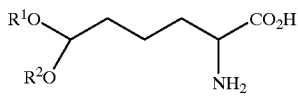

(1)

(wherein R¹ and R² are the same or different, and each of them represents an alkyl group having 1 to 8 carbon atoms, or they combinedly form a ring and represent an alkylene group having 2 to 8 carbon atoms) to a mixture of a 2-oxo-6,6-dialkoxyhexanoic acid of the following general formula (2):

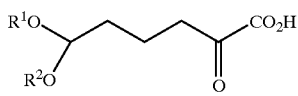

(2)

(wherein R¹ and R² are as defined above) and an L-allysine acetal of the following general formula (3):

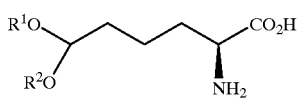

(3)

(wherein R¹ and R² are as defined above) by reacting in the presence of an enzyme capable of stereoselective oxidative deamination of D-amino acids and;

isolating said L-allysine acetal after said converting.

2. The method for producing an L-allysine acetal according to claim 1 wherein the D,L-allysine acetal is D,L-allysine ethylene acetal.

3. The method for producing an L-allysine acetal according to claim 1 wherein the enzyme capable of stereoselective oxidative deamination of D-amino acids is an enzyme derived from a strain of microorganism of the genus Trigonopsis or an enzyme derived from porcine kidney.

4. The method for producing an L-allysine acetal according to claim 1, wherein the reaction is conducted in the presence of a catalase.

5. The method for producing an L-allysine acetal according to claim 1, wherein the reaction is conducted in the presence of a metal oxide.

6. The method for producing an L-allysine acetal according to claim 5 wherein the metal oxide is a manganese oxide.

7. The method for producing an L-allysine acetal according to claim 2 wherein the enzyme capable of stereoselective oxidative deamination of D-amino acids is an enzyme derived from a strain of microorganism of the genus Trigonopsis or an enzyme derived from porcine kidney.

8. The method for producing an L-allysine acetal according to claim 2 wherein the reaction is conducted in the presence of a catalase.

9. The method for producing an L-allysine acetal according to claim 3 wherein the reaction is conducted in the presence of a catalase.

10. The method for producing an L-allysine acetal according to claim 2 wherein the reaction is conducted in the presence of a metal oxide.

11. The method for producing an L-allysine acetal according to claim 3 wherein the reaction is conducted in the presence of a metal oxide.

12. The method for producing an L-allysine acetal according to claim 4 wherein the reaction is conducted in the presence of a metal oxide.

* * * * *